United States Patent [19]

Simpson et al.

[11] Patent Number: 5,698,977
[45] Date of Patent: Dec. 16, 1997

[54] EDDY CURRENT METHOD FOR FATIGUE TESTING

[75] Inventors: John W. Simpson, Tabb; James P. Fulton, Hampton; Russell A. Wincheski, Williamsburg; Ronald G. Todhunter, Grafton; Min Namkung, Yorktown, all of Va.; Shridhar C. Nath, Gaithersburg, Md.

[73] Assignee: The United States of America as represented by the Administrator of the National Aeronautics and Space Administration, Washington, D.C.

[21] Appl. No.: 490,441

[22] Filed: Jun. 5, 1995

Related U.S. Application Data

[62] Division of Ser. No. 134,444, Oct. 12, 1993, abandoned.

[51] Int. Cl.[6] .................... G01N 27/90; G01N 3/32; G01N 19/08; G01R 33/12
[52] U.S. Cl. .................... 324/209; 73/799; 73/810; 324/225; 324/240; 324/242; 324/262
[58] Field of Search .................... 324/209, 225, 324/237, 238, 240–243, 262; 73/577, 578, 799, 808, 810, 811, 813

[56] References Cited

U.S. PATENT DOCUMENTS

| | | | |
|---|---|---|---|
| 3,918,299 | 11/1975 | Donnadieu | 73/799 |
| 4,316,146 | 2/1982 | Jilken | 324/209 |
| 4,689,558 | 8/1987 | Ruuskanen et al. | 324/209 |
| 4,755,753 | 7/1988 | Chern | 324/240 X |
| 5,339,031 | 8/1994 | Chern | 324/262 X |
| 5,423,223 | 6/1995 | Weinstock | 324/209 X |

*Primary Examiner*—Gerard R. Strecker
*Attorney, Agent, or Firm*—Robin W. Edwards

[57] ABSTRACT

Flux-focusing electromagnetic sensor using a ferromagnetic flux-focusing lens simplifies inspections and increases detectability of fatigue cracks and material loss in high conductivity material. A ferrous shield isolates a high-turn pick-up coil from an excitation coil. Use of the magnetic shield produces a null voltage output across the receiving coil in presence of an unflawed sample. Redistribution of the current flow in the sample caused by the presence of flaws, eliminates the shielding condition and a large output voltage is produced, yielding a clear unambiguous flaw signal.

Maximum sensor output is obtained when positioned symmetrically above the crack. By obtaining position of maximum sensor output, it is possible to track the fault and locate the area surrounding its tip. Accuracy of tip location is enhanced by two unique features of the sensor; a very high signal-to-noise ratio of the probe's output resulting in an extremely smooth signal peak across the fault, and a rapidly decaying sensor output outside a small area surrounding the crack tip enabling the search region to be clearly defined. Under low frequency operation, material thinning due to corrosion causes incomplete shielding of the pick-up coil. Low frequency output voltage of the probe is therefore a direct indicator of thickness of the test sample.

Fatigue testing a conductive material is accomplished by applying load to the material, applying current to the sensor, scanning the material with the sensor, monitoring the sensor output signal, adjusting material load based on the sensor output signal of the sensor, and adjusting position of the sensor based on its output signal.

7 Claims, 9 Drawing Sheets

EDDY CURRENT METHOD FOR FATIGUE TESTING

This is a divisional of application Ser. No. 08/134,444 filed on Oct. 12, 1993, now abandoned.

ORIGIN OF THE INVENTION

The invention described herein was jointly made by employees of the United States Government and contract employees during the performance of work under NASA contracts and is subject to the provisions of Section 305 of the National Aeronautics and Space Act of 1958, as amended, Public Law 85-568 (72 Stat. 435; 42 U.S.C. 2457) and 35 USC 202 in which the contractor elected not to retain title.

BACKGROUND OF THE INVENTION

The present invention relates generally to a device and method for detecting material flaws using the eddy current principle, and more particularly to a flux focusing eddy current probe having separate excitation and pick-up coils, magnetically isolated from one another by a highly permeable flux focusing lens, for detecting different types of flaws or discontinuities at various depths within an electrically conductive material, and an automated method of monitoring crack growth rate and trajectory during fatigue testing. The automated method is not limitative and the invention can also be used for manual testing and fault isolation. The eddy current probe of this invention is simple in construction and operation while providing unambiguous signals of fault indication simplifying support equipment requirements, supporting self nulling capability in no fault conditions during surface fault detection negating the need for calibration standards, maintaining highly resistant lift-off characteristics, and providing highest signal levels at fault tips.

The use of eddy currents to inspect electrically conductive material for flaws is known in the art. Such methods are particularly useful in the non-destructive evaluation of conducting material for surface or internal faults and material thinning. An eddy current probe generally consists of a coil electrically connected to a current generator producing an alternating current within the coil. This generates a time-varying primary magnetic field which in turn induces current flow (eddy currents) in an electrically conductive material positioned in the vicinity of the coil. As described by Lenz's Law, the eddy currents, during their return path, create an opposing secondary magnetic field superimposed on the coil's primary magnetic field decreasing the coil's flux and modifying the coil's voltage effecting the impedance of the coil.

The eddy current's power and direction are dependent upon the specific impedance of the conductive material. In unflawed conditions, eddy current flow is generally parallel to the magnetizing coil's windings. Flaws, such as cracks, pits, and material thinning, in the conductive material create regions of higher resistances at the flaw location which affect eddy current flow. The direction change in eddy current flow reduces the opposing secondary magnetic field and consequently the voltage in the coil. An impedance detecting circuit, which may take the form of an inductive bridge, monitors coil voltage which, if different from an established no-fault condition, indicates a conductive material flaw. Sharp changes in impedance over a localized area would indicate the existence of cracks or other relatively small area flaws, whereas gradual changes in impedance over a broad region of the conductive material might indicate large-area flaws such as a grain change in the metal, an area of material creep, or material thinning. Though traditional eddy current probes use the same coil for magnetizing the conductive material and for detecting impedance variations caused by changes to eddy current flow, use of separate magnetizing and pick-up coils is known in the prior art. The same principle, however, of monitoring for variations in coil impedance as indicative of a conductive material flaw is applied. This conventional eddy current flaw detection technique often involves complex impedance planes necessitating special test electronics to achieve null balancing and known standards to calibrate probe responses to each type of flaw.

Multiple coils within a single probe can be used as separate magnetizing and sensing means, or they may be used in a more traditional fashion and independently operate the coils as bi-function magnetizing-sensing coils. In the case of a multiple coil probe, the coils can be juxtaposed in a matrix to provide a large detection area, or concentrically arranged to simultaneously detect flaws at various depths. Each coil of multiple coil probes is energized and monitored for impedance variations independently. Multiple coil probes use a shielding material high in magnetic permeability to provide a low reluctance path and divert potentially interfering magnetic fields to separate the coils from one another. The shielding is designed to isolate all interfering signals so that each coil's impedance can be independently balanced. This design provides an ability to perform material testing at several frequencies simultaneously. The conventional eddy current flaw detection techniques are employed which require special test equipment to analyze probe signals.

As the conventional eddy current probe separates from the test material, the eddy currents induced within the material rapidly decrease resulting in a similarly decreasing opposing magnetic field which directly affects the resistance and inductance of the probe's coil. Abrupt changes occur to the impedance balance being monitored for fault indications making traditional eddy current probes unusable during these lift-off conditions.

In addition to detecting existing flaws in conductive material, determination of fatigue crack growth criteria in structural materials is important to predict material fatigue failure limits. Current approaches to testing fatigue cracking include optical methods and other length measuring techniques such as crack mouth opening displacement gauge and four point potential drop method. Each of these procedures requires long periods of continuous monitoring by well trained operators to record fatigue crack tip locations and to adjust experimental controls in compliance with experimental designs. Though the crack mouth opening displacement gauge and four point potential drop method could potentially be automated to reduce operator time requirements, only overall crack length data can be provided and the fatiguing process must usually be stopped to make the crack length measurements.

Eddy current devices have also been used to monitor fatigue crack growth during fatigue. This approach to monitoring fatigue crack growth has been automated, though, again, only overall crack length data can be provided. The traditional eddy current probe which implements impedance measurement techniques to identify the presence of test material faults is not conducive to tracking the crack tip which supports crack trajectory as well as crack growth rate.

OBJECTS

Therefore, it is an object of the present invention to overcome or mitigate these problems and to provide a flux-focusing eddy current probe whose fault detection characteristics provide unambiguous fault detection signals enhancing the confidence level of fault detection and reducing the need for special test electronics. Through the use of the present invention, a flux-focusing characteristic of probe signals during surface fault detection eliminates the need for known standards of specific types of flaws. Further, a single probe design and instrument configuration performs surface and subsurface eddy current fault detection.

It is a further object of the invention to establish a method which supports automated monitoring of faults in conducting material. The use of this method will perform continuous tracking and archiving of fatigue crack growth rates and trajectory during the fatigue process as well as automatically controlling conducting material loading conditions based on measured fatigue data and experimental designs.

SUMMARY OF THE INVENTION

The present invention is directed to a flux-focusing eddy current probe that satisfies the need for unambiguous signals of fault detection, reducing the need for special test equipment. The flux-focusing eddy current probe performs non-destructive evaluation of electrically conductive material. The probe uses an excitation coil to induce eddy currents in conducting material perpendicularly oriented to the coil's longitudinal axis. A separate pick-up coil, surrounded by the excitation coil, is used to detect generated fields. Between the excitation coil and pick-up coil is a flux focusing lens which magnetically separates the two coils and produces high flux density at the outer edge of the pick-up coil.

The present invention is further directed to an automated eddy current system that satisfies the need to perform continuous fatigue testing. This system performs fatigue evaluation of conducting material and is dependent upon the use and characteristics of the flux-focusing eddy current probe. A computer interprets the signal from the probe to control the probe's position over the conducting material and to control the loading of the conducting material under test. A method for performing the automated testing requires a load to be applied to the conducting material to produce a fault. The flux-focusing eddy current probe scans the conducting material and signals the computer once a fault is detected. The computer then adjusts the loading on the material and position of the probe to continue the test to completion.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1:
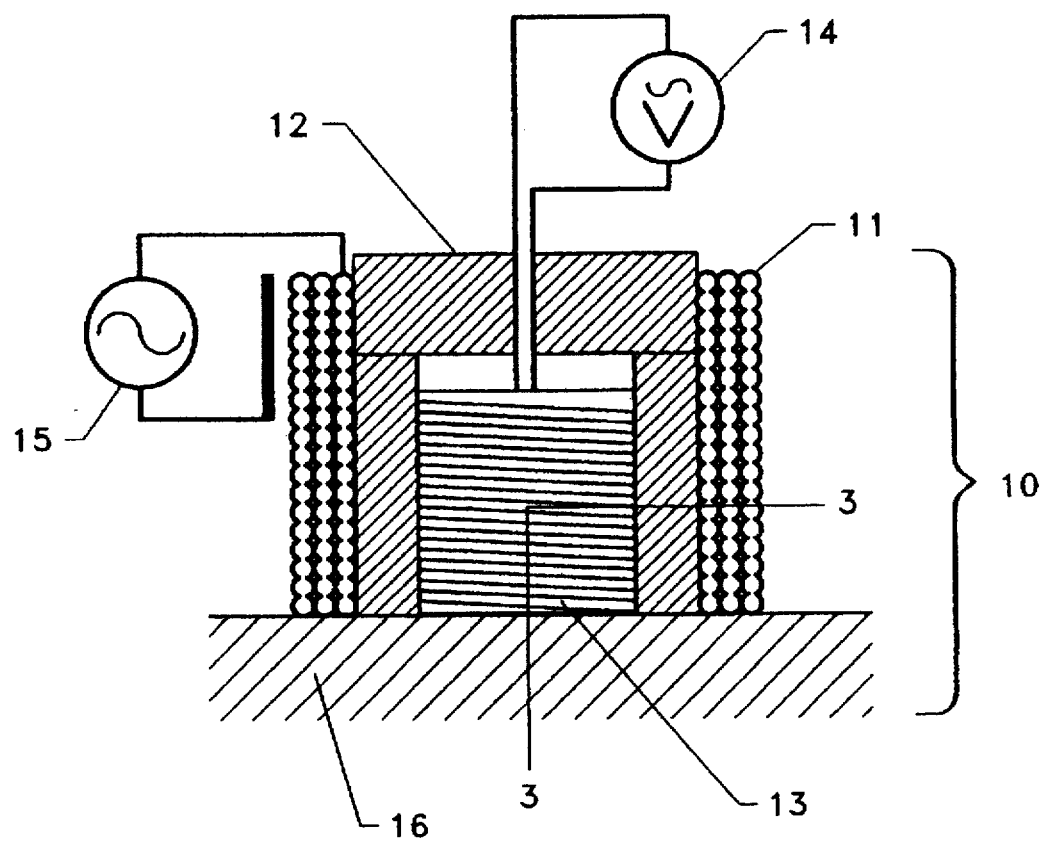
FIG. 1 shows a cross sectional view across line 1—1 of FIG. 2 for an elevation view of a flux-focusing eddy current probe constructed in accordance with the principles of this invention.

With reference now to FIG. 1, wherein like numbers designate like components throughout all the several figures, the flux-focusing eddy current probe of the invention is particularly well adapted for non-destructive evaluation, and for fatigue testing of electrically conductive material. The flux-focusing eddy current probe generally designated at 10 includes an excitation coil, a flux focusing lens, and a pick-up coil. The probe 10 applies the eddy current principle to evaluate electrically conductive material 16 for faults. An alternating current supplied by a current source 15 electrically connected to the excitation coil 11 produces eddy currents within conductive material 16 placed in proximity with the probe 10. Magnetic fields created in the pick-up coil 13 are registered by an A.C. voltmeter 14 electrically connected to the pick-up coil 13. The flux focusing lens 12 magnetically separates the excitation coil 11 from the pick-up coil 13 and produces high flux density at the edge of the pick-up coil 13.

Figure 2:
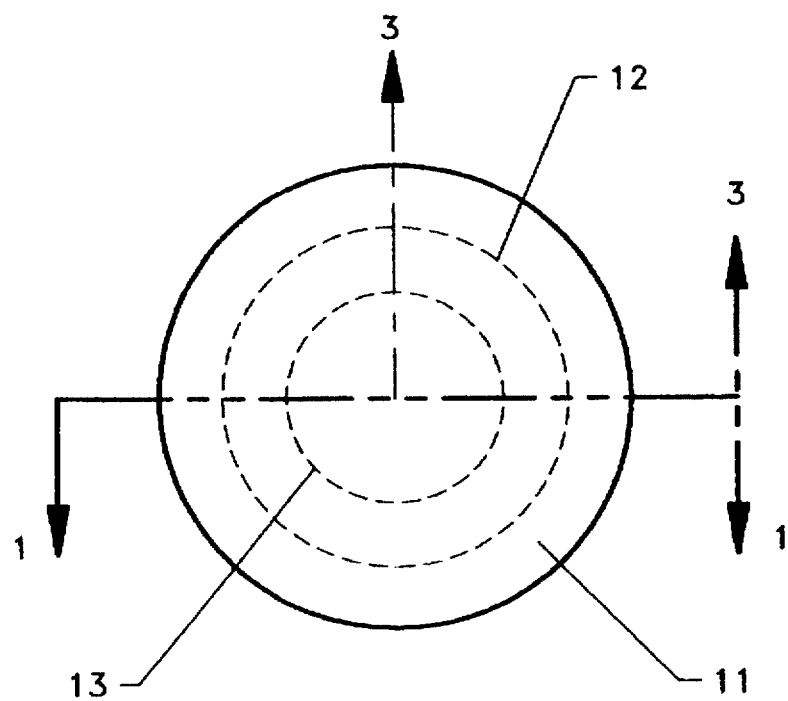
FIG. 2 shows a plan view of the flux-focusing eddy current probe illustrated in FIG. 1 with the receiving coil shown in phantom.

With reference now to FIG. 2, the excitation coil 11, the flux focusing lens 12, and the pick-up coil 13 are circular and concentrically arranged with the excitation coil 11 at the exterior of the probe 10, the pick-up coil 13 at the innermost position of the probe 10, and the flux focusing lens 12 between the coils 11 and 13. The overall size of the probe 10 is primarily determined by the diameter of the flux focusing lens 12 which is a function of fault depth and fault isolation accuracy. The diameter of the lens 12 is minimized to reduce the overall size of the probe 10 and to provide accurate location information of identified faults, though it must be of sufficient size to support test frequencies of the applied current from the current source 15 and to maximize search area covered by the probe. Likewise, the thickness of the flux focusing lens is minimized to ensure energy created by the magnetic field of the excitation coil 11 produces energy in the pick-up coil 13 when the probe 10 is in free space or a flaw in the conductive material 16 crosses the boundary established by the lens 12, though the lens 12 must provide isolation from direct magnetic energy of the excitation coil 11 from producing an alternating current in the pick-up coil 13 when the probe 10 is in contact with unflawed conductive material 16. Direct energy transfer is avoided when the len's thickness is several times the skin depth of the magnetic flux within the lens. The size of the pick-up coil 13 is simply maximized to achieve the largest possible surface area for greatest signal sensitivity within the constraints dictated by the excitation coil 11 and the flux focusing lens 12. It must be noted, however, that the smallest detectable flaw is approximately equal in size to one-half the inner diameter of the flux-focusing lens 12.

Figure 3A:
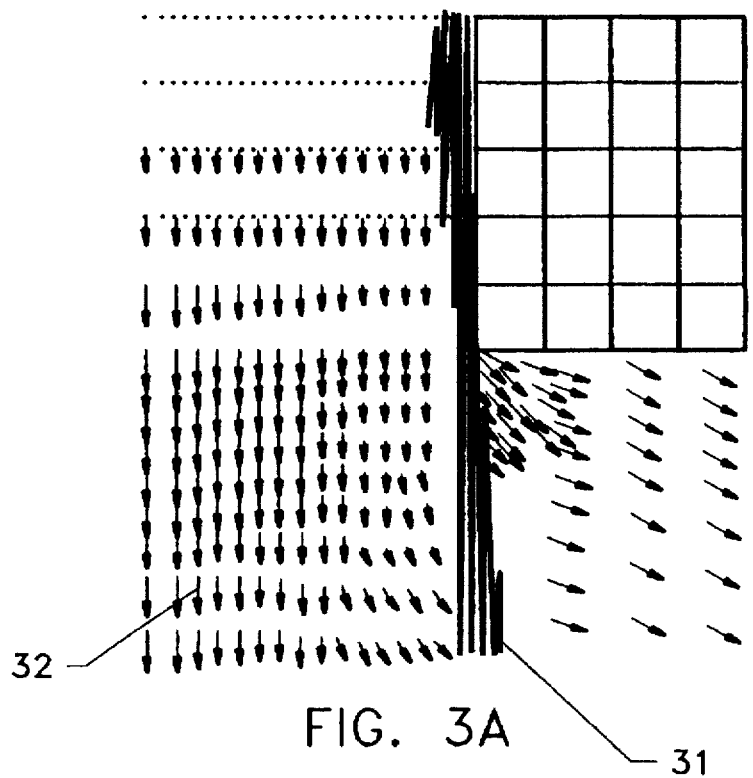
FIG. 3A shows a cross sectional view across line 3—3 of FIGS. 1 and 2 of the magnetic flux lines when the flux-focusing eddy current probe is energized in free space.
Figure 3B:
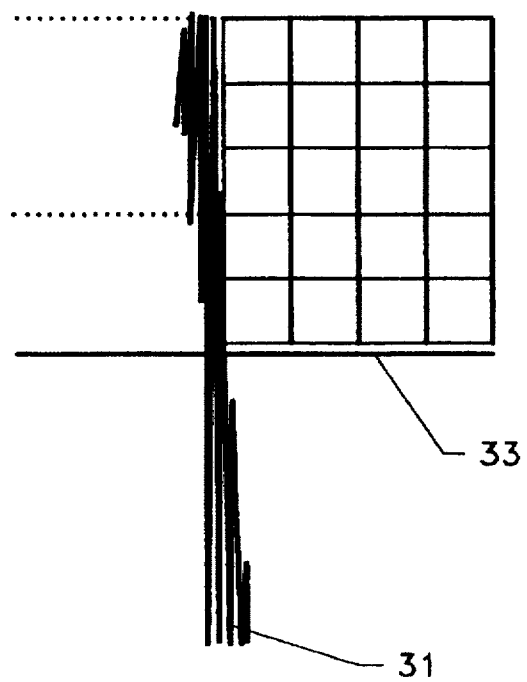
FIG. 3B shows a cross sectional view across line 3—3 of FIGS. 1 and 2 of the magnetic flux lines when the flux-focusing eddy current probe is energized and in contact with an unflawed electrically conductive material.
Figure 4A:
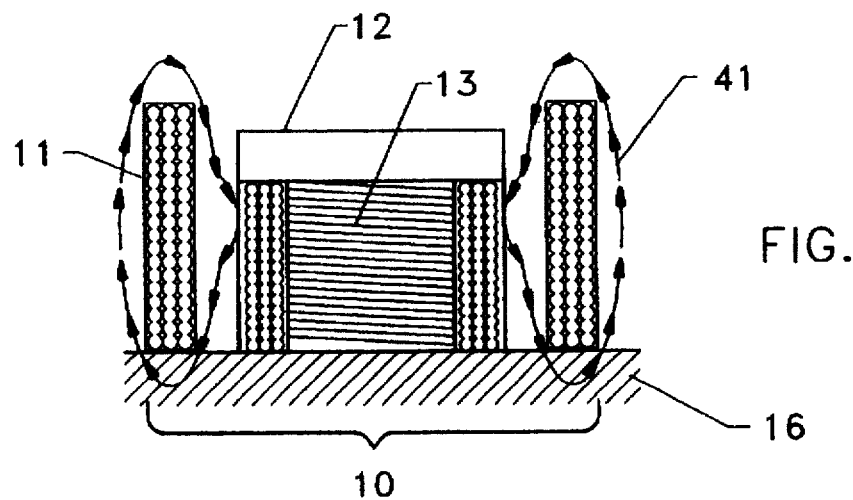
FIG. 4A shows an elevation view for the magnetic field of the excitation coil which generates eddy currents in conductive material as focused by the ferromagnetic lens.
Figure 4B:
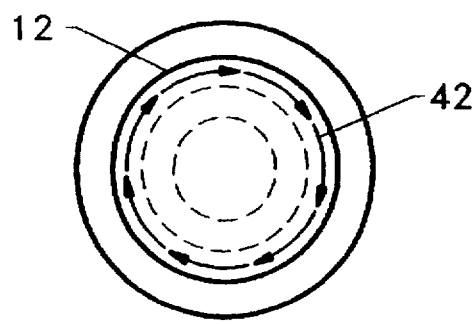
FIG. 4B shows a plan view of the eddy current flow in unflawed electrically conductive material.

With reference now to FIGS. 3, 4 and 5, an alternating current applied to the excitation coil 11 creates a magnetic field 41 which in turn creates eddy currents within conductive material 16, FIG. 4A. The depth of penetration of the magnetic field 41 into the test material 16 is dependent upon the conductivity of the material 16 and the frequency of the applied current source. Consequently, the frequency of the drive signal is predetermined by the type of inspection being performed. Inspection for surface breaking flaws requires high frequency so as to concentrate the eddy currents at the surface of the material, whereas inspection for interior or back surface flaws requires low frequency such that the skin depth of the induced currents penetrate to the desired depth.

The magnetic field 41 is also established in the flux focusing lens 12. The lens 12 is formed of conducting material high in magnetic permeability which provides a low reluctance path to divert the magnetic field away from the pick-up coil 13. The point of maximum penetration of the concentrated magnetic field 41 within the lens 12 is at one half the height of the excitation coil 11, FIG. 4A. In the preferred embodiment, the top of the pick-up coil 13 falls below this maximum penetration point.

In the absence of a conducting material test sample 16, some leakage of the magnetic flux 31 around the lens 12 results, FIG. 3A. The leakage flux 32 produces a current in the pick-up coil 13 which provides a signal, FIG. 5B, to the A.C. voltmeter. When the probe is placed above a non-flawed electrically conductive surface, however, a complete electromagnetic separation of the pick-up coil 13 from the excitation coil 11 can be achieved, FIG. 3B. The flux 33 is concentrated within the conductive material 16 and generates eddy currents 42, FIG. 4B. The induced eddy currents 42 work to stop any change in the magnetic state of the system so that the leakage field within the interior of the flux focusing lens 12 is canceled, resulting in a null signal, FIG. 5A, to the A.C. voltmeter.

Figure 4C:
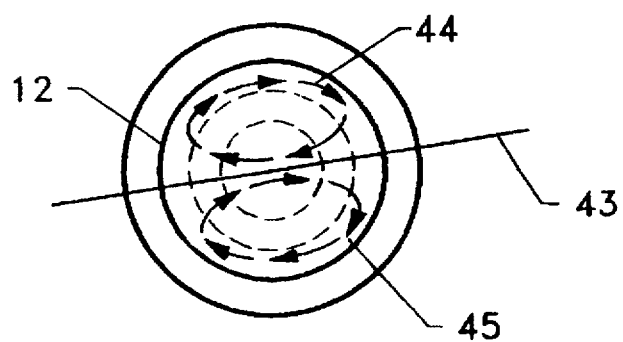
FIG. 4C shows a plan view of the eddy current flow in flawed electrically conductive material where the flaw divides the probe's circumference.
Figure 4D:
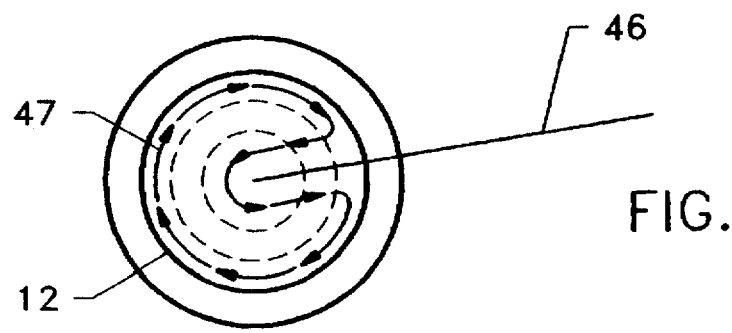
FIG. 4D shows a plan view of the eddy current flow in flawed electrically conductive material where the flaw tip lies within the probe's circumference.
Figure 5A:
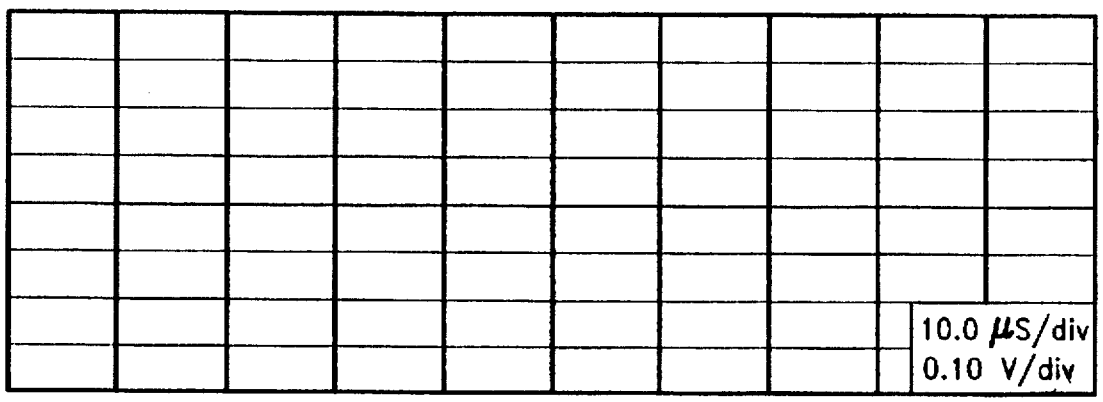
FIG. 5A shows a flux-focusing eddy current probe's signal level response for a 50 KHz, 10.0 V p-p excitation coil signal when the probe is in contact with an unflawed aluminum alloy plate.
Figure 5B:
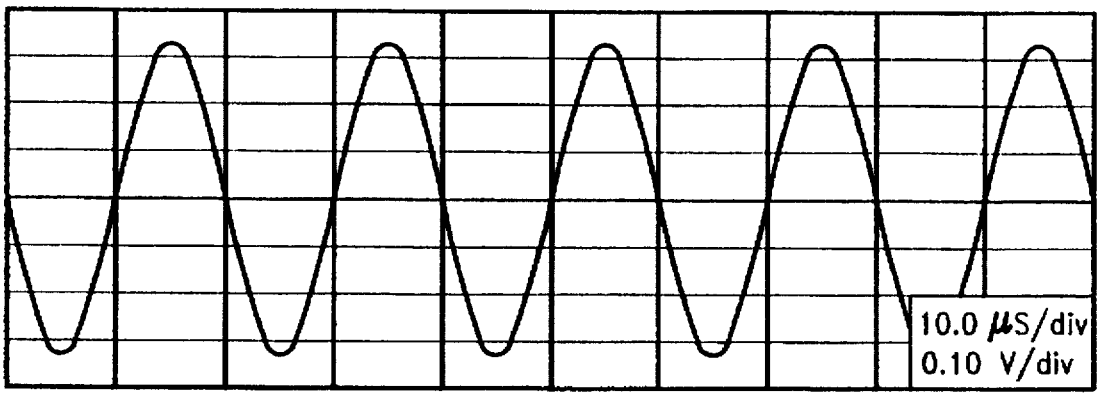
FIG. 5B shows a flux-focusing eddy current probe's signal level response for a 50 KHz, 10.0 V p-p excitation coil signal when the probe is in free space.
Figure 5C:
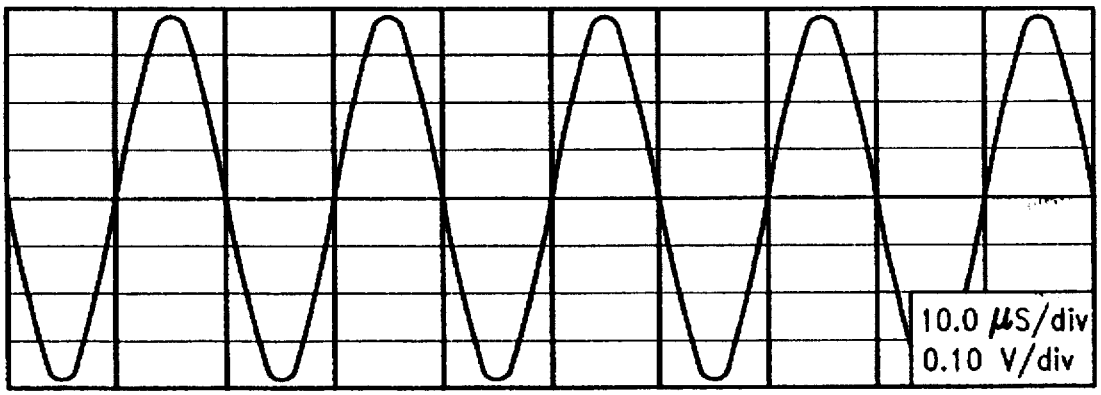
FIG. 5C shows a flux-focusing eddy current probe's signal level response for a 50 KHz, 10.0 V p-p excitation coil signal when the probe is in contact with a flawed aluminum alloy plate.
Figure 6A:
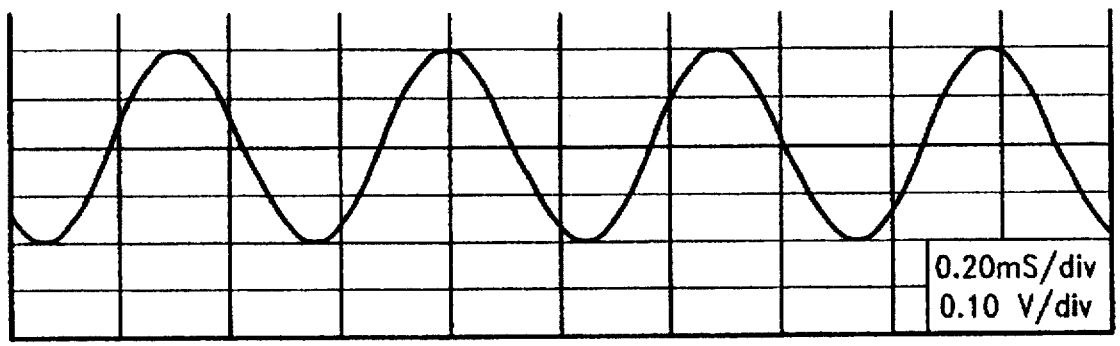
FIG. 6A shows a flux-focusing eddy current probe's signal level response for a 2 KHz, 10.0 V p-p excitation coil signal when the probe is in contact with a 2 mm unflawed aluminum alloy plate.
Figure 6B:
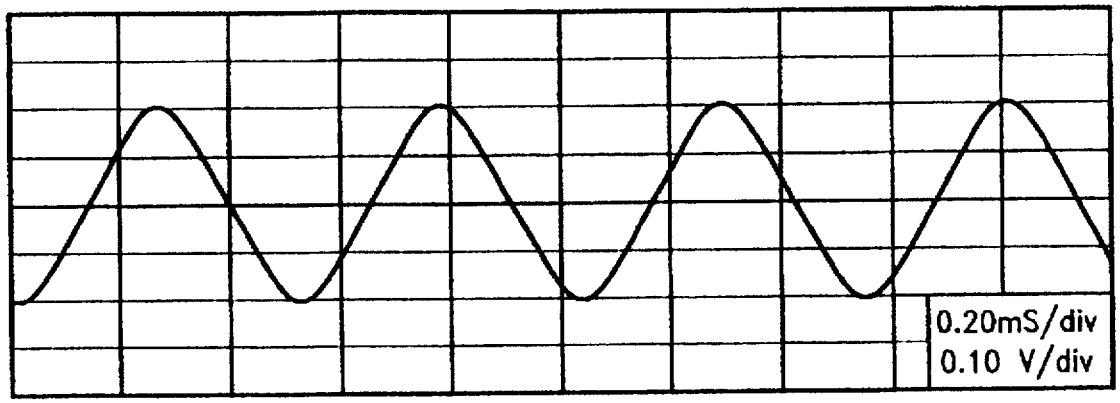
FIG. 6B shows a flux-focusing eddy current probe's signal level response for a 2 KHz, 10.0 V p-p excitation coil signal when the probe is in contact with a 1 mm unflawed aluminum alloy plate.
Figure 6C:
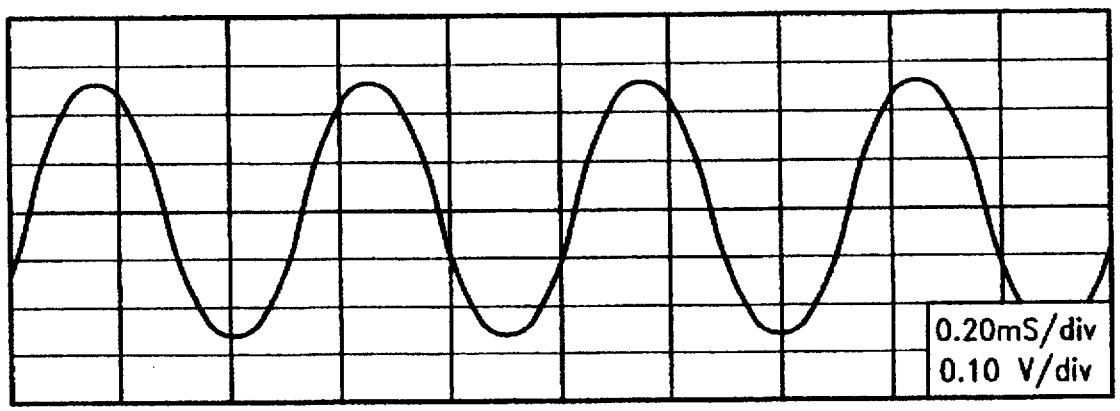
FIG. 6C shows a flux-focusing eddy current probe's signal level response for a 2 KHz, 10.0 V p-p excitation coil signal when the probe is in free space.
Figure 6D:
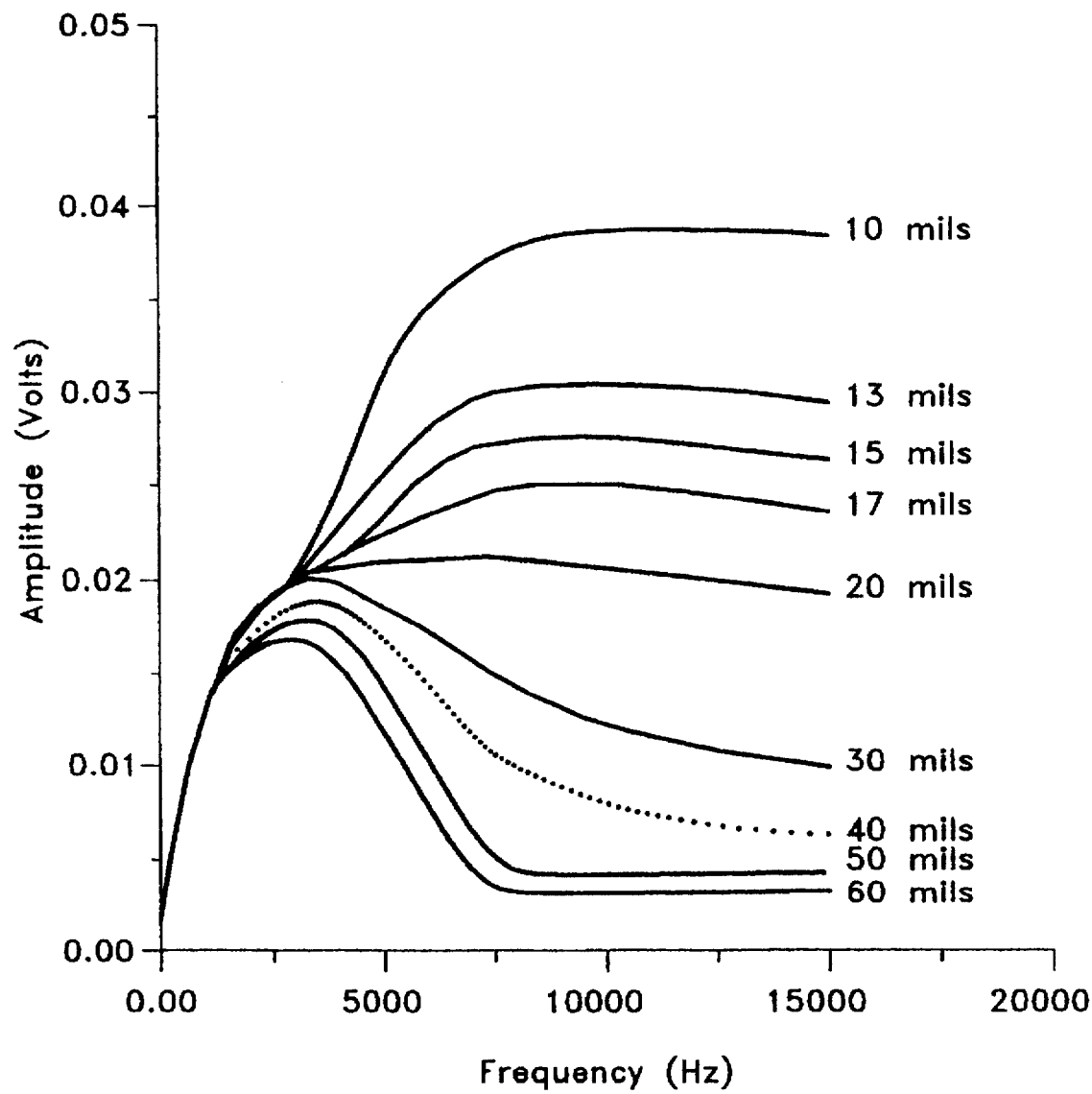
FIG. 6D shows a flux-focusing eddy current probe's signal level response to thickness variations in aluminum as a function of frequency.

In the presence of a conductive material fault 43 which divides the area covered by the probe 10, a change in eddy current flow results, FIG. 4C. The field produced by the eddy currents 44 and 45 pass through the area of the pick-up coil resulting in an alternating current being established in the pick-up coil 13. The presence of a current in the pick-up coil 13 provides an unambiguous voltage signal as indicative of the presence of a conductive material fault. Where the tip of a fault 46 falls within the area covered by the pick-up coil 13, FIG. 4D, the field produced by eddy current flow 47 is additive to the field of the excitation coil 11 and is greater than that produced by in air leakage flux 32 resulting in a higher voltage signal level, FIG. 5C, thus providing a maximum signal level.

With reference now to FIG. 6, operation of the flux-focusing eddy current probe at reduced frequencies increases the penetration of the magnetic field and supports evaluation of conductive material thickness variations. As material thins, eddy currents in the conducting material are directed to within the area covered by the pick-up coil producing a voltage increase in the coil. Consequently, decreased material thickness produces increased flux-focusing eddy current probe output levels. The output level is directly related to the thickness of a specific material allowing measurement of the material's actual thickness.

Figure 7:
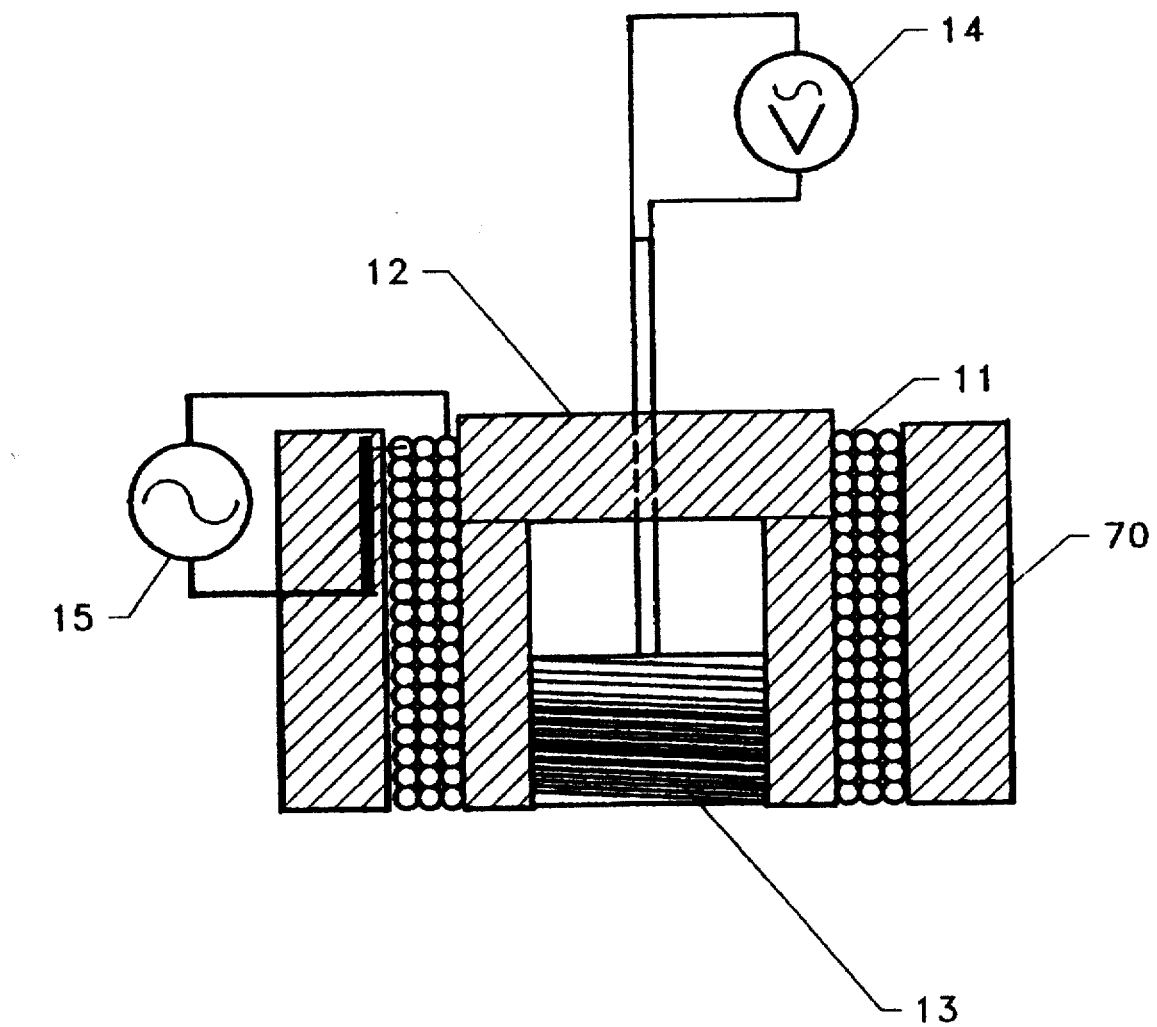
FIG. 7 shows another version of the flux-focusing eddy current probe embodying features of the present invention which provides additional resistance to edge effects and other conductive material discontinuities.

With reference now to FIG. 7, an alternate probe configuration supports detecting faults close to an edge of the conductive material under test or near other conductive material discontinuities. An exterior shield 70 made of conductive material high in magnetic permeability focuses magnetic flux around the outside edge of the probe to prevent eddy currents from reflecting off a nearby conductive material edge and into the area of the pick-up coil. This allows the flux-focusing eddy current probe to be used near conductive material edges, however, the exterior shield 70 reduces the probe's overall sensitivity performance.

Figure 8A:
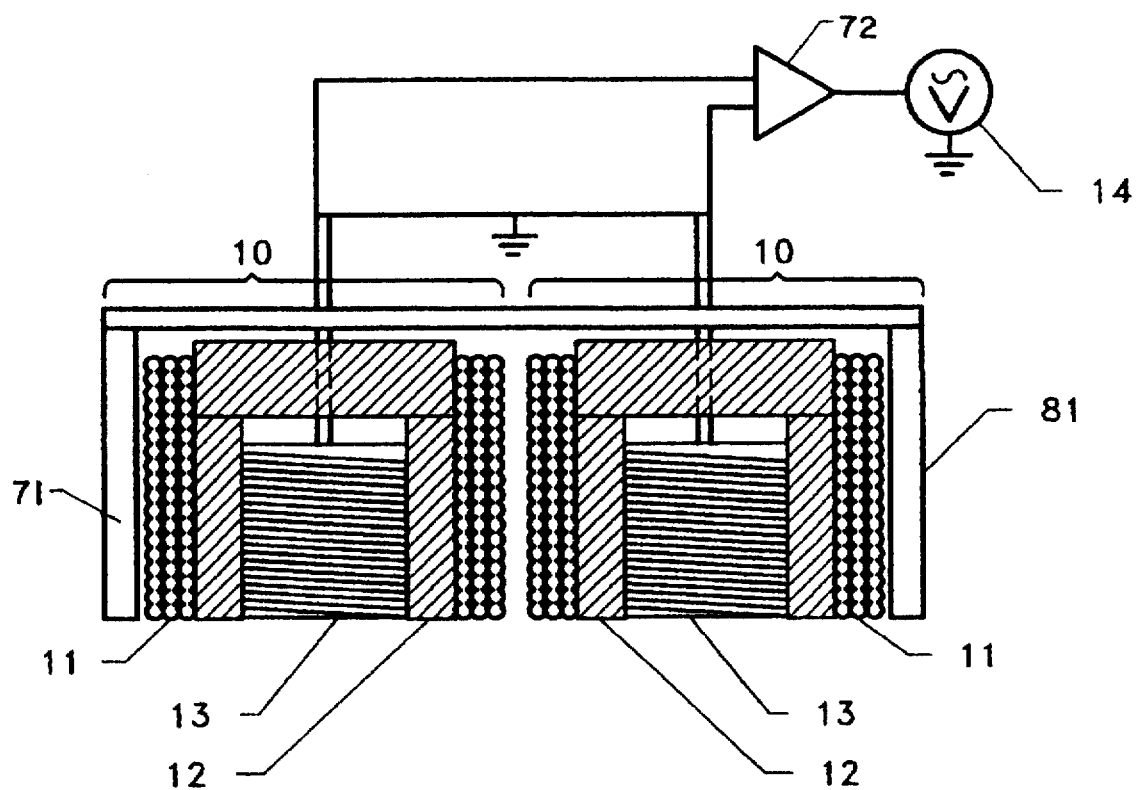
FIG. 8A shows another version of the flux-focusing eddy current probe embodying features of the present invention which provides additional resistance to lift-off response indicating conductive material fault.
Figure 8B:
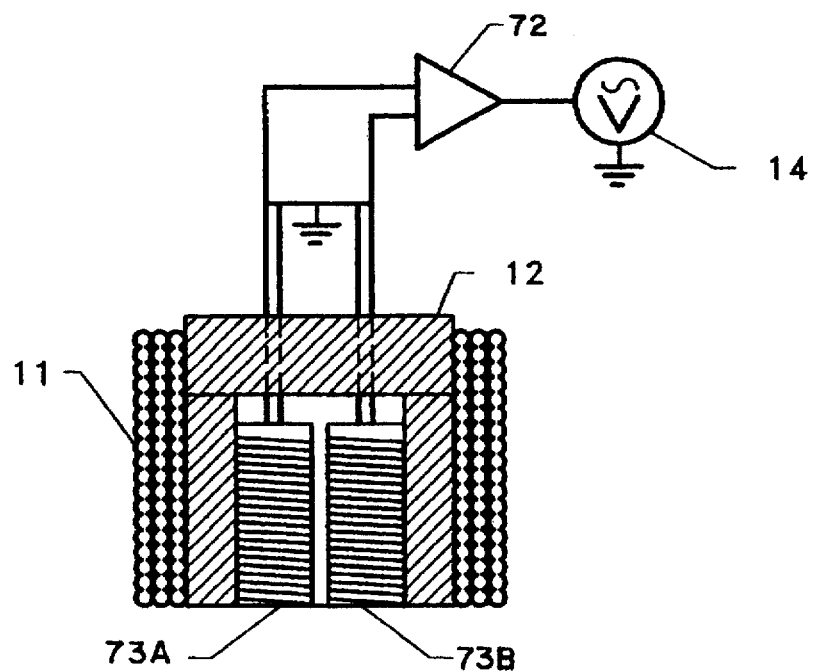
FIG. 8B shows another version of the flux-focusing eddy current probe embodying features of the present invention which provides additional resistance to lift-off response indicating conductive material fault.

With reference now to FIG. 8, though the preferred embodiment is resistant to lift-off problems, alternate probe configurations are possible which provide further protection from lift-off conditions incorrectly indicating the presence of a conductive material fault. In the alternate embodiments, signals from a plurality of probes 10 combined within a casing 81, FIG. 8A, or a plurality of pick-up coils 73A and 73B within a single excitation coil 11 and flux focusing lens 12, FIG. 8B, are compared to one another. Equal, non-zero signal levels signify probe lift-off from the test material. Pick-up coils 13 or 73A and 73B are electrically connected to a differential amplifier 72. Lift-off conditions result in equal signal level outputs such that the difference is zero and no fault indication is provided by the A.C. voltmeter 14.

Figure 9:
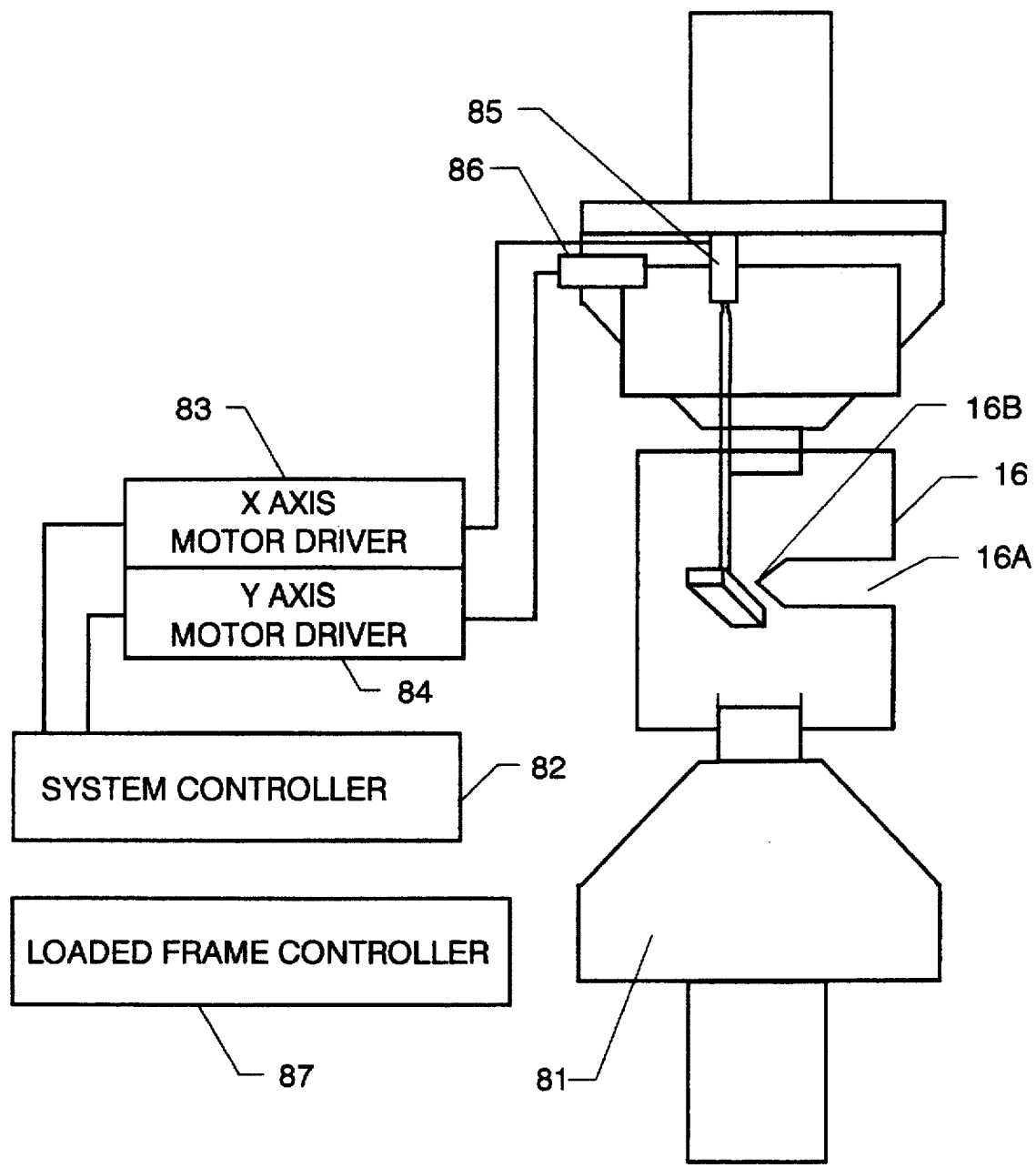
FIG. 9 shows the eddy current probe system for locating crack tips.

With reference now to FIG. 9, the eddy current probe system for fatigue evaluation of conductive material incorporates the flux-focusing eddy current probe 10 as a means of tracking fatigue crack growth in a conductive material 16 installed in a load frame 81. The unambiguous flaw signal of the eddy current probe supports automated computer searching and identifying fatigue cracks. The probe 10 is used to scan conductive material 16 installed in the load frame 81. A computer 82 controls the probe's location over the conductive material by means of x-axis 83 and y-axis 84 motor drives which power their respective stepping motors 85 and 86. Additionally, the computer 82 continuously monitors the output of the probe 10 as it is scanned about the stress riser 16B in the sample and directs the load frame controller 87 as it cyclically fatigues the conductive material sample.

The area of the probe scan is initiated around a notch 16A in the conductive material sample. This location gives rise to high stress concentrations as the sample undergoes fatigue. Upon detection of crack growth, a large output signal from the probe 10 is received by the computer 82. The computer adjusts the position of the probe such that it is centered about the region of crack initiation. As the crack continues to grow, the computer updates the probe's position to trace the fatigue crack tip throughout the fatigue process. The position of the crack tip is determined by the peak output level of the probe as the crack path is traversed. The peak search routine using an algorithm similar to the grid-search chi-square minimization scheme increments the probe's location in the direction of the crack growth as determined by previous crack tip locations. The scan is continued until the new crack tip is found. Upon locating the crack tip, the probe is moved a short distance back along the path of the crack and the search is repeated. By continuously reevaluating the path of the crack near the crack tip, errors in crack tip location due to signal noise and crack branching are avoided. As the crack grows to predetermined lengths, experimental parameters such as the load level applied to the conductive material sample are adjusted by the computer. This method allows for completely automated experimental control of fatigue studies which saves time, allows continuous unattended testing, and archives fatigue growth rates and trajectories.

Although our invention has been illustrated and described with reference to the preferred embodiment thereof, we wish to have it understood that it is in no way limited to the details of such embodiment, but is capable of numerous modifications for many mechanisms, and is capable of numerous modifications within the scope of the appended claims.

What is claimed as new and desired to be secured by Letters Patent of the United States is:

1. A method of testing fatigue in a conductive material comprising the steps of:
    (a) applying a load to the conducting material;
    (b) applying a current to an eddy current probe to generate eddy currents within the conducting material;
    (c) scanning the conducting material with the eddy current probe;
    (d) monitoring the output signal of the eddy current probe;
    (e) adjusting the load on the conducting material based on the output signal of the eddy current probe; and
    (f) adjusting the x-axis and y-axis position of the eddy current probe over the surface of the conducting material based on the output signal of the eddy current probe, wherein the position of the fatigue crack tip is determined by maximum eddy current probe output signal and the position of the eddy current probe is incremented in the direction of the crack growth as determined by previous crack tip locations.

2. The method of testing fatigue in a conducting material as recited in claim 1, wherein the load applied to the conducting material constitutes a tensile force.

3. The method of testing fatigue in a conducting material as recited in claim 1, wherein the load applied to the conducting material constitutes a compressive force.

4. The method of testing fatigue in a conducting material as recited in claim 1, wherein the load applied to the conducting material is applied cyclically.

5. The method of testing fatigue in a conducting material as recited in claim 1, wherein the conducting material has a notch.

6. The method of testing fatigue in conducting material as recited in claim 5, wherein the scanning step begins near the notch in the conducting material.

7. The method of testing fatigue in a conducting material as recited in claim 6, wherein a controlling means archives fatigue crack growth rates and fatigue crack trajectories.

* * * * *